US00RE35339E

United States Patent [19]

Rapoport

[11] E Patent Number: Re. 35,339

[45] Reissued Date of Patent: Oct. 1, 1996

[54] METHOD AND APPARATUS FOR THE TREATMENT OF OBSTRUCTIVE SLEEP APNEA

[75] Inventor: David M. Rapoport, New York, N.Y.

[73] Assignee: New York University, New York, N.Y.

[21] Appl. No.: 936,675

[22] Filed: Aug. 28, 1992

Related U.S. Patent Documents

Reissue of:

[64] Patent No.: 5,065,756
Issued: Nov. 19, 1991
Appl. No.: 136,293
Filed: Dec. 22, 1987

[51] Int. Cl.[6] ..... A61M 16/00

[52] U.S. Cl. ..... 128/204.18; 128/205.25; 128/205.24; 128/207.13

[58] Field of Search ..... 128/204.18, 204.21, 128/204.23, 205.25, 205.24, 207.13

[56] References Cited

U.S. PATENT DOCUMENTS

| | | | |
|---|---|---|---|
| 1,632,449 | 6/1927 | McKesson | 128/207.13 |
| 2,675,803 | 4/1954 | Kaslow | 128/205.25 |
| 4,263,908 | 4/1981 | Mizerak | 128/205.25 |
| 4,266,540 | 5/1981 | Panzik et al. | 128/205.25 |
| 4,328,797 | 5/1982 | Rollins, III et al. | 128/205.25 |
| 5,109,839 | 5/1992 | Blasdell et al. | 128/204.18 |
| 5,117,819 | 6/1992 | Servidio et al. | 128/204.18 |

OTHER PUBLICATIONS

12 Single-Sided 8½x11 Pages of Respironics Inc. Sales Literature (some pages dated Aug. 1, 1986).

1 Double-Sided 8½x11 Page of Respironics Inc. Sleep Easy™ Nasal CPAP Sanders' CPAP Circuit Operating Instructions dated Sep. 16, 1986 on second side.

1 Double-Sided 8½x14 Page of Respironics Inc. Sleep Easy™ Nasal CPAP Sanders' CPAP Circuit Operating Instructions dated Jan. 4, 1988 on second side.

Respironics, SleepEasy Sanders' CPAP circuit, alleged to be 1987.

Respironics, Inc., SleepEasy II, Nasal CPAP System, Clinical Instruction manual, alleged to be 1987.

Respironics, Inc., SleepEasy II, Nasal CPAP System, Dealer Service Manual, aleged to be 1987.

Practice of Sleep Disorders Medicine—State of the Art 1987, ASDC/ISS Annual Meeting, Sep. 10–13, 1987, San Francisco, CA.

Practice of Sleep Disorders Medicine—State of the Art 1987, ASDC/CSS, Annual Meeting, Sep. 10–13, 1987, San Francisco, CA.

Nasal Airway Positive Pressure in Patients with Occlusive Sleep Apnea, Methods and Feasibility, James A. Sterline, Bjorn Thorarinsson, and Samuel T. Kuna, (pp. 1152–1155).

*Continuous Positive Airway Pressure,* A new system, M. A. Branthwaite, I. C. W. English and E. A. Shinebourne, Anaesthesia, 1974, vol. 29, pp. 326–334.

NightBird Nasal CPAP System Instruction Manual, alleged to be Mar. 1987.

—Continuous Positive Airway Pressure: A Breathing System To Minimize Respiratory Work—David R. Hillman, FFARACS: Kevin E. Finucane, FRACP, vol. 13, No. 1., Jan., 1985.

*Primary Examiner*—Aaron J. Lewis
*Attorney, Agent, or Firm*—Rosen, Dainow & Jacobs

[57] ABSTRACT

A method and apparatus for the treatment of obstructive sleep apnea wherein a continuous positive pressure is supplied to a nose mask from a threshold valve via a flexible tube, and air is discharged from the mask via vent holes in the mask for rapid discharge of exhaled air.

15 Claims, 1 Drawing Sheet

METHOD AND APPARATUS FOR THE TREATMENT OF OBSTRUCTIVE SLEEP APNEA

Matter enclosed in heavy brackets [ ] appears in the original patent but forms no part of this reissue specification; matter printed in italics indicates the additions made by reissue.

This invention relates to a method and apparatus for the treatment of obstructive sleep apnea and is particularly directed to such a method and apparatus wherein a positive pressure is applied to the nares of a patient by means of a nose mask.

The syndrome of obstructive sleep apnea is a common disorder, especially in middle-aged obese males. The problem arises in sleep-induced occlusion of the oropharyngeal airway, resulting in multiple apneic occurrences during sleep. As a consequence, there is a severe interruption of sleep in the patient, and, as the disease progresses over periods of time, greater degrees of asphyxia occur. The duration of apnea may exceed two minutes, with the arterial hemoglobin oxygen saturation falling below 50%. The patient may be entirely unaware of the occurrence of these frequent obstructions to breathing. The symptoms are generally excessive day-time sleepiness, and snoring. The nocturnal asphyxia may eventually lead to a number of further problems, such as cardiac arrhythmia, pulmonary hypertension and right heart failure, systemic hypertension severe morning headache intellectual and personality changes, and polycythemia.

One method of treatment for the disease is a tracheostomy, which is left open at night. Medical and psychosocial problems frequently interfere with the acceptance of a tracheostomy, both by the patient and the physician, and this solution has generally been employed only in severe cases. Patients have frequently chosen to accept the discomfort associated with the disease rather than have a tracheostomy.

It has been suggested that continuous positive airway pressure (CPAP) be applied to the patient, during periods of sleep, by way of the nose ("Reversal of Obstructive Sleep Apnea by Continuous Positive Airway Pressure Applied Through the Nares", Colin Sullivan, et al., The Lancet, Apr. 18, 1981, pp. 862–865). Sullivan et al. suggest the application of low levels of pressure, in the range of 4.5 to 10.0 centimeters $H_2O$, and reported that this procedure completely prevented upper airway occlusion during sleep. The continuous positive airway pressure applied in this manner may provide a pneumatic splint for the nasopharyngeal airway.

In the arrangement provided by Sullivan et al., two soft plastic tubes were shaped to fit snugly in each naris. The other ends of these tubes were inserted into a light-weight wide-bore tube, the arrangement being strapped to the patient's face. A medical grade silicone rubber was then run over the nose and nares to provide a seal. Continuous positive pressure was produced by connecting one end of the wide-bored tube to an air compressor motor with variable speed control. The other end of the side-bore tube was led away from the patient and narrowed, to provide a mechanical resistance. The resistance of the circuit was chosen so that a high bias flow (20–40 liters/minute) was sustained for the range of pressures required at the nose.

While the CPAP procedure as reported by Sullivan et al. may provide temporary relief, i.e., patients with severe disease may satisfactorily employ the technique for several nights, the required cumbersome physical equipment renders this solution satisfactory only for in-hospital management of patients, hence being practical only for severely affected patients. The discomfort of this device is not conducive to continual use by patients in the home environment.

While various masks have been employed in the past for respiration purposes, conventional respiration masks also cover the mouth and are designed primarily for temporary use or for use by persons who do not require comfort. Such masks may be employed for anesthesia or resuscitation. A full face mask of this type is not satisfactory for patients with obstructive sleep apnea. Treatment of obstructive sleep apnea relies on the difference in pressure between the nose and the mouth to open the airway. Furthermore, leaving the mouth uncovered allows the patient to breathe normally while awake and in case of failure of the air compressor or valve. Comfort is critical, since willingness on the part of a patient to continually employ a mask during sleeping hours defeats the purpose of the treatment.

In other masks, such as provided, for example, for dental applications, the nose masks have face seals such that they can not be pressurized. Application of CPAP absolutely requires the maintenance of pressure.

In one solution to this problem, as disclosed in U.S. Pat. No. 4,655,213 an improved apparatus for the application of CPAP is comprised of a comfortable nose mask, for the treatment of apnea, whereby patients experience no discomfort from the use of the mask. In this apparatus, a nose mask is provided incorporating a threshold valve, wherein the air pressure continually applied to the mask is continually released from the mask, by means of a valve, at such a pressure that normally some pressurized air always escapes from the mask by way of the valve. This feature serves to maintain the air pressure at the nose, in order to maintain the nasopharyngeal airway open, as well as to provide a continuous flow of fresh air to the mask so that the patient may exhale through the mask, with the exhaled air being immediately exhausted through the valve.

An apparatus of the type disclosed in U.S. Pat. No. 4,655,213, as illustrated in FIG. 1, is comprised of a generally cup-shaped nose piece 10 provided with a rim 11 for lightly sealing the mask to the face. The rim 11 is preferably an air cuff, i.e., a flexible doughnut-shaped member, fitted to the edge of the mask and containing a pressurized gas. It is, of course, apparent that other sealing rims may be employed for the mask.

The nose mask is further provided with a valve assembly 12 including a bypass valve 13 for continually relieving air within the mask at a pressure such that the valve normally will not be closed in use. In addition, the valve assembly 12 has an extension 14 adapted to be connected to an air supply tube 15, the tube 15 receiving compressed air from a conventional compressor 16. The nose piece 10 is connected to the valve assembly 12 by way of a swivel interconnection 19.

In order to hold the nose mask on the face of the patient, lightweight flexible straps 17 may be connected to the mask to extend around the head of the patient.

Since the threshold valve employed in this mask may be a very simple device, it may be readily miniaturized, so that the mask assembly may be very small and lightweight, thereby being comfortable to wear. The air supply tube may be a single small, very flexible tube, enabling the patient to move around at night without difficulty. Ease of movement when using this mask is further enhanced by the provision of a swivel joint at the junction of the valve and mask.

While the apparatus of U.S. Pat. No. 4,655,213 thus constitutes a substantial improvements over prior solutions, it is desirable to further improve the apparatus, to render its use even more satisfactory to patients.

SUMMARY OF THE INVENTION

Briefly stated, in accordance with the invention, the mask is coupled to the compressor or blower by way of a flexible tube, but a valve is not provided on the mask itself. Instead, a relief valve is connected to the flexible tube, preferably adjacent the compressor or blower, so that it may be mounted at a position separated from the patient and mask. In addition, in accordance with the invention, one or more ports are provided on the mask itself to enable the continuous venting of the mask at a predetermined rate.

Removal of the valve from the mask, in accordance with the invention, enhances the patient' comfort and gives greater freedom of movement.

In order that the invention will be more clearly understood, it will now be disclosed in greater detail, with reference to the accompanying drawings, wherein.

DESCRIPTION OF THE PREFERRED EMBODIMENTS

Figure 1:
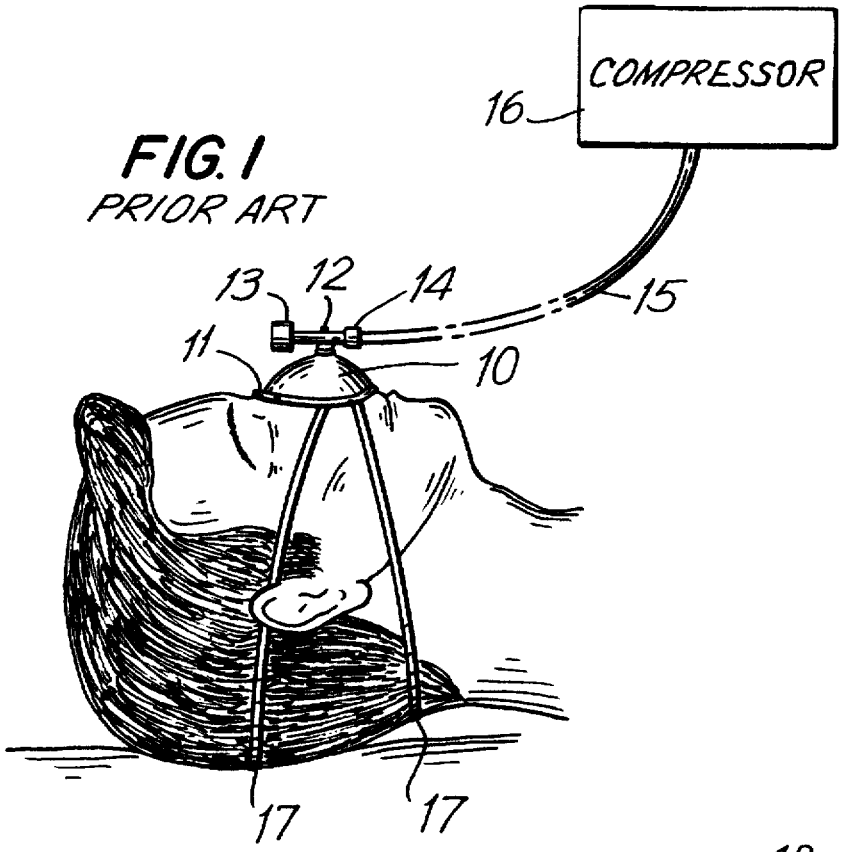
FIG. 1 PRIOR ART
FIG. 1 is a view of a patient wearing a known mask.
Figure 2:
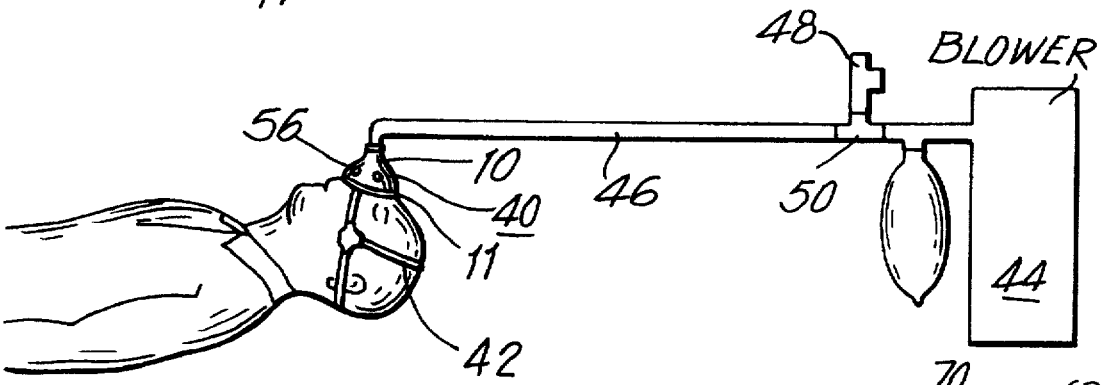
FIG. 2 is a simplified illustration of an apparatus in accordance with the invention.

Referring now to FIG. 2, therein is illustrated an apparatus in accordance with the preferred embodiment of the invention. A mask *or nose fitting* 40, suitable for fitting over the nose of the patient, may be generally similar to that shown and described with reference to FIG. 1, includes a nose piece 10 and rim 11 for sealing the mask to the face. Thus, the air cuff seal 11 is of a lightweight plastic material and must be of a non-irritating material, since it is in continuous contact with the face of the patient. The nose piece 10 is of a plastic material that is partially rigid and partially flexible, such as heavy vinyl, of a nature that can conform to the face. The element must be sufficiently large to accommodate the noses of all patients who may employ the mask. The partial rigidity is required so that the nose piece will generally maintain its shape in use, while still enabling it to conform to the face of the patient.

A harness 42 maintains the mask in position on the patient when the apparatus is used. In the arrangement in accordance with the invention, however, the mask 40 is connected directly to a compressor or blower 44 by a hollow flexible tube 46. An adjustable relief valve *in the form of a threshold valve or pressure controller* 48 is connected between the blower 44 and the mask 40 at a T fitting 50 inserted in the tube 46. The valve is mounted by any convenient conventional means at a location separated from the patient and mask, the flexible tube being sufficiently long that fixed mounting of the valve has no effect on movements of the patient.

Figure 3:
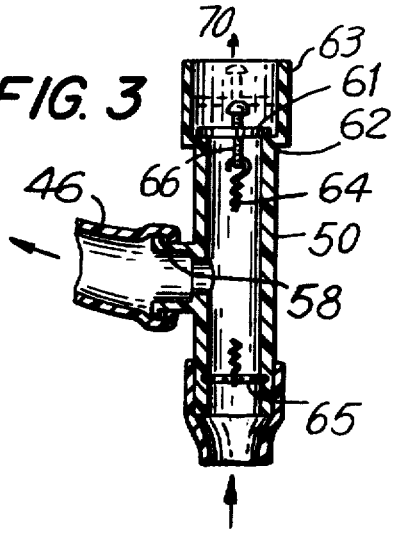
FIG. 3 is a cross-sectional view of a mask that may be employed in the apparatus of FIG. 2.

As illustrated in FIG. 3, the valve 48 may be simply comprised of a rigid valve disk 61 held adjacent a valve seat 62 formed at one end of the T fitting 50. The disk 30 may be loosely axially guided at its edge by an enlarged diameter end extension 63 on the end of the T fitting. The valve disk 61 is urged toward the valve seat 62 by a spring, such as helical spring 64 extending through the T fitting 50 to a fixed connection, for example, to a pin 65 held to the walls of the T fitting. Adjustability of the pressure maintained by the valve may be effected by connecting the end of the spring 64 to the end of an adjustment screw 66 threaded in the disk 61. The adjustment of the screw thereby controls the tension of the spring, to determine the pressure of air directed to the mask. The valve is settable to enable the production of an operating pressure range within the mask from 5.0 to 15.0 centimeters $H_2$). The pressure adjustment for any patient is set so that under normal breathing conditions the valve is always open, even during inhalation. As a result, the required positive pressure is always present to maintain the nasopharyngeal airway opened.

It is of course apparent that the illustrated valve constitutes only the preferred embodiment thereof and that other constructions thereof for serving this function may alternatively be employed in accordance with the invention. The valve 48 continually discharges gases to the external atmosphere as indicated by the arrow 70 when the blower 44 provides a positive pressure in the system. The valve 48 is suitable to maintain a positive pressure within the system to 5 to 15 centimeters of water with a discharge of air flow from the valve 48 in the range of 30 to 50 liters per minute.

A reservoir bag 54 connected to the flexible tube 46 between the valve 48 and blower 44 serves to reduce transients in the flow rate and pressure within the system.

Figure 4:
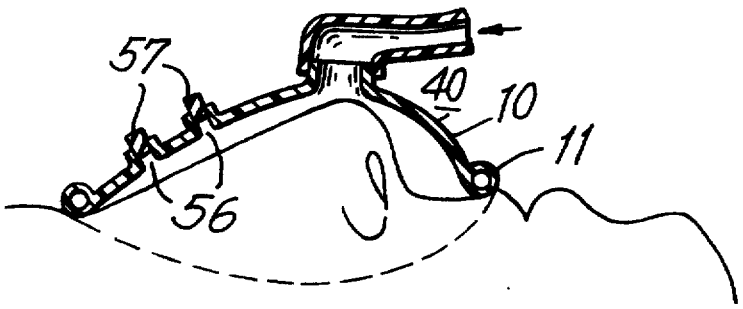
FIG. 4 is a cross sectional view of a relief valve that may be encorporated in the apparatus of FIG. 2.

As illustrated in FIGS. 2 and 4, the mask 40 includes ports, preferably two ports 56 passing through the shaped portion 10 of the mask 40. Through these ports 56 air from the system, and particularly air exhaled by the patient, passes from the system to the external ambient environment. These ports 56 constitute intentional leaks at the mask, and must be small enough not to vent off all the pressure delivered by the compressor 44/valve 48 combination, but must be large enough to vent the patient's expired breath over the period of expiration. For example, holes which are individually capable of passing a flow of 5 to 7 liters of air per minute with an internal mask pressure of 5 centimeters of water in material, and having a diameter in the order of 1/16 inch thick, have been found satisfactory. Suitable means for blocking one or both of these ports, such as plugs 57, may be provided in order to enable adjustment of the rate of air discharge from the mask. It is of course apparent that the invention is not limited to this size and number of ports.

When the pressure within the mask is at the low end of the operating range, that is in the range of 5–7 centimeters of water, at least two ports 56 with sizing as described above are left open to vent the mask at a rate of approximately 10–12 liters per minute. When the pressure within the mask is set in the upper end of the range, from 10–15 centimeters of water, one hole is plugged while the other provides a vent which delivers in the order of 5–7 liters per minute.

Since the valve 48 is not mounted on the mask, but is coupled thereto by a flexible tube, the weight of the mask assembly that must be supported on the patient's face is substantially reduced, and the comfort to the patient is accordingly greatly increased. The connection between the rube 46 and the mask 40 may be via a swivel joint 58, if desired, to permit the patient to have more freedom of movement without danger of entangling the mask apparatus with the bedding or causing the mask to separate from the face.

The compressed air may be provided by any conventional device, so that the patient may inexpensively provide this source for use in his own home. It is preferred, however, that a blower be provided instead of a compressor, since compressors tend to dessicate the air supply, while blowers deliver air at room humidity, can handle ultrasonically humidified air, and drop flow upon increases in back pressure. This latter feature is desirable, since the flow from a blower quickly increases during inspiration, when the back pressure increases in the system. The compressed air may be heated and humidified by conventional devices.

In the treatment of obstructive apnea, it must be stressed that the condition can be expected to continue for the remainder of the patient'life, and it can be expected to increase in severity. Accordingly, a patient seeking relief by the use of CPAP can expect to require use of the mask for the remainder of his life. Effectiveness of CPAP treatment depends upon the willingness of the patient to use a nose mask. The nose mask should be employed during naps as well as during nighttime sleeping.

the present invention therefore solves t he problem of providing the comfort required of such a nose mask, thereby minimizing the reluctance of patients to seek relief by this method. The mask in accordance with this invention may be readily employed in the patient's home and provide an inexpensive solution to the problem of obstructive sleep apnea.

While various nose masks are known and have been used for respiration, none combine the features of maintaining continuous positive air pressure at the nose and continuous bypass of air away from the nose through vents that are always open when the mask is in use, even during inhalation It is this combination of features which is most effective in treating obstructive sleep apnea.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An assembly for treatment of obstructive sleep apnea comprising:

a nose mask adapted to be fitted over the nose of a patient;

supply means coupled to said mask for supplying air with continuous positive pressure to said mask suited to maintain the nasopharynegeal airway of a patient open when said supply means is supplied with gas at positive pressure, said supply means comprising an elongated flexible tube coupled at one end to said mask and having an opposite and remote from said mask that is connected to inlet means for receiving pressurized air and delivering air to said flexible tube to establish within the mask a predetermined range of pressures;

venting means located on the nose mask for continuously venting patient expiratory flow while said positive pressure is applied to said mask via said supply means; and a threshold valve mounted at said opposite end of the flexible tube and adjustable for maintaining a positive pressure within said mask in the range of about 5 to 15 centimeters water at all times when said mask is fitted over the nose of a patient for respiration.

2. An assembly as claimed in claim 1 wherein said venting means comprises in the mask at least one vent hole spaced from the coupling of the tube to the mask.

3. An assembly as claimed in claim 2 wherein said gas is air and said at least one vent hole vents air in the range of 5–15 liters/minute for internal mask pressures in the range of 5–15 centimeters water.

4. An assembly as claimed in claim 3 wherein said at least one vent hole comprises two vent holes each venting air in the range of about 5–7 liters/minute for internal mask pressures in the range of 5–15 centimeters water.

5. An assembly as claimed in claim 4 wherein said vent holes are each closable by means of a plug.

6. In the method for the treatment of obstructive sleep apnea comprising supplying air of a continuous positive pressure within a pressure range of 5–15 centimeters water via a long flexible tube to a nose mask to maintain the nasopharyngeal airway of a patient open, the improvement comprising controlling the pressure in the nose mask by means of a threshold valve connected to the tube at a position remote from the mask, and continuously venting air, including patient expiratory air, directly from said mask via at least one hole in said mask, at a rate of 5–15 liters/minute.

7. A method as claimed in claim 6 wherein when the pressure in the nose mask is controlled by the threshold valve to a value in the range of =b 5–7centimeters water, the continuous venting step is carried out at a rate of approximately 10–12 liters/minute, and when the pressure in the nose mask is increased to a value in the range of 10–15 centimeters water, the continuous venting is of the order of 5–7 liters/minute.

*8. An assembly for treatment of obstructive sleep apnea comprising:*

*a nose mask adapted to be fitted over the nose of a patient;*

*supply means coupled to said mask for supplying air with continuous positive pressure to said mask suited to maintain the nasopharyngeal airway of a patient open when said supply means is supplied with gas at positive pressure, said supply means comprising an elongated flexible tube coupled at one end to said mask and having an opposite end remote from said mask that is connected to inlet means for receiving pressurized air and delivering air to said flexible tube to establish within the mask a predetermined range of pressures;*

*venting means located on the nose mask for continuously venting patient expiratory flow while said positive pressure is applied to said mask via said supply means; and*

*means mounted at said opposite end of the flexible tube and adjustable for maintaining a positive pressure within said mask in the range of about 5 to 15 centimeters water at all times when said mask is fitted over the nose of a patient for respiration.*

*9. An assembly for treatment of obstructive sleep apnea comprising:*

*a nose means adapted to be fitted to the nose of a patient for sealing off the nose;*

*supply means coupled to said nose means for supplying air with continuous positive pressure to said nose means suited to maintain the nasopharyngeal airway of a patient open when said supply means is supplied with gas at positive pressure, said supply means comprising an elongated flexible tube coupled at one end to said nose means and having an opposite end remote from said nose means that is connected to inlet means for receiving pressurized air and delivering air to said flexible tube to establish within the nose means a predetermined range of pressures;*

*venting means located on the nose means for continuously venting patient expiratory flow while said positive*

*pressure is applied to said nose means via said supply means; and*

*means mounted at said opposite end of the flexible tube and adjustable for maintaining a positive pressure within said nose means in the range of about 5 to 15 centimeters water at all times when said nose means is fitted to the nose of a patient for respiration.*

*10. An assembly for treatment of obstructive sleep apnea comprising:*

*a nose means adapted to be fitted to the nose of a patient for sealing off the nose;*

*supply means coupled to said nose means for supplying air with continuous positive pressure to said nose means suited to maintain the nasopharyngeal airway of a patient open when said supply means is supplied with gas at positive pressure, said supply means comprising an elongated flexible tube coupled at one end to said nose means and having an opposite end remote from said nose means that is connected to inlet means for receiving pressurized air and delivering air to said flexible tube to establish within the nose means a predetermined range of pressures;*

*venting means located on the nose means for continuously venting patient expiratory flow while said positive pressure is applied to said nose means via said supply means; and*

*means mounted at said opposite end of the flexible tube and adjustable for maintaining a positive pressure within said nose means all times when said nose means is fitted to the nose of a patient for respiration.*

*11. An assembly for treatment of obstructive sleep apnea, comprising:*

*a nose fitting for sealing off the nose of a patient;*

*an air supply coupled to said nose fitting for supplying air with continuous positive pressure to said nose fitting suited to maintain the nasopharyngeal airway of a patient open when said air supply is supplied with air at a positive pressure, said air supply comprising an elongated flexible tube coupled at one end to said nose fitting and having an opposite end that is connected to an inlet for receiving pressurized air and delivering air to said flexible tube to establish within said nose fitting a predetermined range of pressures;*

*at least one vent associated with said nose fitting for continuously venting patient expiratory flow while said positive pressure is applied to said nose fitting via said air supply; and*

*a pressure controller located at said opposite end of said flexible tube and adjustable for continuously maintaining a positive pressure within said nose fitting when said nose fitting is fitted to the nose of a patient for respiration.*

*12. An assembly for treatment of obstructive sleep apnea, comprising:*

*a nose fitting for the nose of a patient for sealing off the nose;*

*an air supply coupled to said nose fitting for supplying air with continuous positive pressure to said nose fitting suited to maintain the nasopharyngeal airway of a patient open when said air supply is supplied with air at a positive pressure, said air supply comprising an elongated flexible tube coupled at one end to said nose fitting and having an opposite end that is connected to an inlet for receiving pressurized air and delivering air to said flexible tube to establish within said nose fitting a predetermined range of pressures;*

*at least one vent associated with said nose fitting for continuously venting patient expiratory flow while said positive pressure is applied to said nose fitting via said air supply; and*

*a pressure controller located at said opposite end of said flexible tube and adjustable for continuously maintaining a positive pressure within said nose fitting in the range of about 5 to 15 centimeters water when said nose fitting is fitted to the nose of a patient for respiration.*

*13. An assembly for treatment of obstructive sleep apnea comprising:*

*a nose mask adapted to be fitted over the nose of a patient;*

*supply means coupled to said mask for supplying air with continuous positive pressure to said mask suited to maintain the nasopharynegeal airway of a patient open when said supply means is supplied with gas at positive pressure, said supply means comprising an elongated flexible tube coupled at one end to said mask and having an opposite end remote from said mask that is connected to inlet means for receiving pressurized air and delivering air to said flexible tube to establish within the mask a predetermined range of pressures;*

*a pressure controller mounted at said opposite end of the flexible tube and adjustable for maintaining a positive pressure within said mask in the range of about 5–15 centimeters water at all times when said mask is fitted over the nose of a patient for respiration;*

*at least one continuously open vent hole located on the nose mask for continuously venting patient expiratory flow while said positive pressure is applied to said mask via said supply means, said vent hole being small enough not to vent off all of the positive pressure supplied by the supply means while at the same time being large enough to vent the patient's expired air over the period of expiration.*

*14. An assembly for treatment of obstructive sleep apnea as claimed in claim 13, wherein said vent hole is located on the mask such that the incoming pressurized air carries the patient's expired air through the vent hole.*

*15. A method for the treatment of a patient suffering from obstructive sleep apnea, comprising:*

*(a) supplying air at a continuous positive pressure within a pressure range of about 5–15 centimeters water via a long flexible tube to means fitted to the nose of the patient for sealing off the nose to maintain the nasopharyngeal airway of the patient open,*

*(b) controlling the positive pressure in the means fitted to the nose by a pressure controller connected to the flexible tube at a position remote from the mask,*

*(c) continuously venting air, including patient expiratory air, directly from said means fitted to the nose via at least one hole associated with said means fitted to the nose while said air at a continuous positive pressure is being supplied to the means fitted to the nose of the patient,*

*(d) said at least one hole associated with said means fitted to the nose of the patient being sized such that it does not vent all of the positive pressure supplied via the flexible tube while at the same time venting the patient's expired air over the period of expiration, the air at the positive pressure carrying the patient's expired air through the at least one hole associated with said means fitted to the nose of the patient.*

* * * * *